(12) United States Patent
Anderson

(10) Patent No.: US 8,285,503 B1
(45) Date of Patent: Oct. 9, 2012

(54) BALANCED TWO-CONDUCTOR TIME DOMAIN REFLECTOMETER

(75) Inventor: Scott K. Anderson, Meridian, ID (US)

(73) Assignee: Technical Development Consultants, Inc., Meridian, ID (US)

( * ) Notice: Subject to any disclaimer, the term of this patent is extended or adjusted under 35 U.S.C. 154(b) by 0 days.

(21) Appl. No.: 13/305,363

(22) Filed: Nov. 28, 2011

(51) Int. Cl.
*G01R 29/02* (2006.01)
*G01R 27/00* (2006.01)
*G01R 13/00* (2006.01)

(52) U.S. Cl. ............... 702/79; 702/65; 702/66
(58) Field of Classification Search ........... 702/65, 702/66, 79
See application file for complete search history.

(56) References Cited

U.S. PATENT DOCUMENTS

| | | | |
|---|---|---|---|
| 6,657,443 B2 | 12/2003 | Anderson | |
| 6,831,468 B2 | 12/2004 | Anderson | |
| 2003/0042916 A1* | 3/2003 | Anderson | 324/643 |
| 2004/0059509 A1* | 3/2004 | Anderson et al. | 702/2 |
| 2004/0164746 A1* | 8/2004 | Anderson et al. | 324/640 |
| 2004/0164750 A1* | 8/2004 | Anderson | 324/664 |

* cited by examiner

*Primary Examiner* — Michael Nghiem
(74) *Attorney, Agent, or Firm* — Your Intellectual Property Matters, LLC; Robert A. Frohwerk

(57) ABSTRACT

The described apparatus and methods use Time Domain Reflectometry (TDR) to determine the absolute volumetric moisture content of various media. The effects of dispersion caused by conductive and dielectric properties of the medium on the waveform are extrapolated by detecting the bulk propagation time and the slope of the distorted transition of the characteristic reflected waveform. Fast transitions are injected by a differential step function generator into a two-conductor waveguide, which is immersed in soil or other medium of interest. Unlike previous single-ended TDR systems, a differential digitizer senses the probes. Timing control between the two digitizers is critical. Use of an integrated fully differential system eliminates the need for a coaxial cable and an associated balancing transformer, or balun. This enables a two-conductor probe that is more easily inserted into soil, rather than requiring three conductors. Non-conductive probe tips may be pointed to facilitate insertion without causing measurement ambiguity.

11 Claims, 4 Drawing Sheets

BALANCED TWO-CONDUCTOR TIME DOMAIN REFLECTOMETER

TECHNICAL FIELD

The present invention relates generally to Time Domain Reflectometers, and specifically to sensors of absolute moisture based on time domain reflectometry.

BACKGROUND

Time Domain Reflectometers (TDRs) have proven to be the preferred instruments for the measurement of permittivity in various media, including soils. This popularity arises from the independence of propagation time from the electrical conductivity of the medium. Volumetric water content measurements can be calculated with high confidence from permittivity, using techniques described by Anderson in U.S. Pat. No. 6,657,443, which makes these instruments highly suitable for measuring the moisture environment in the root zone of growing crops. Many other methods of soil water content measurement are plagued by errors attributed to the electrical conductivity of the soil.

A further advantage of TDRs is that they can be inserted into the soil without excavation and thus can gather transpiration data without severely disturbing the delicate transpiration system comprised of the small roots and soil structures around them. This is often a critical requirement for horticultural research and for monitoring the root zone of food crops.

The use of Time Domain Reflectometers has been limited by their high cost. A further drawback has been the impractical deployment of TDR sets in agricultural and research fields due to their coaxial cables and power supply lines which must be strung through the crops. Both of these drawbacks have been resolved with the introduction of an integrated Time Domain Reflectometer wherein the step function generator and waveform digitizer are located immediately at the incident end of the waveguide, as disclosed in U.S. Pat. No. 6,831,468 by Anderson et al.

In that disclosure the waveguide is single-ended. The step function propagates along a single conductor in the presence of a reference ground plane or conductor. Although that 2-conductor waveguide provides a useful propagation path, it lacks balance and does not maximize the volume of medium subjected to the permittivity measurement. In practical systems, the reference ground plane is often divided into two rods parallel to the propagation rod and spaced equally on either side of it, thus forming a 3-rod waveguide. This improves the spatial balance of the propagating wave and facilitates the permeation of additional soil volume in the measured sample. Many traditional TDR probes are fashioned from three rods to achieve these advantages. The coaxial center conductor is wired to the center rod and the sheath is wired to the outer two rods. However, the resulting 3-rod probe is more difficult to insert into the root zone and still is not optimum for sampling volume.

In order to reduce the insertion force in a balanced waveguide and to improve its sampling volume some waveguide probes are built with baluns in them, a balun being a transformer used to convert between a balanced signal and a single-ended one. In other words, these devices convert the unbalanced single-ended coaxial cable into a balanced differential 2-wire transmission line. The waveguide takes the form of two rods with a balanced differential wave propagating on them. The sampled soil volume is improved by about 40% over a 3-rod waveguide having the same width, and the insertion force is reduced considerably.

A disadvantage exists with the 2-rod waveguide. Since the balun is reactive, being an inductive device, it acts as a high pass filter. It cannot propagate the steady state part of the step function. Many researchers depend upon the long-term response of the reflected wave to derive the electrical conductivity of the soil. When a balun is deployed as part of a measurement system, the long-term step response diminishes severely and can easily droop to zero within a few tens of microseconds. Thus, balanced waveguides equipped with baluns have not been deployed where electrical conductivity measurements require high confidence.

The ideal TDR waveguide system would employ all of the following:
1. A balanced differential wave with uniform electromagnetic (EM) field characteristics relative to the poles of the waveguide;
2. No more than two rods for easier insertion and higher sampling volume; and
3. No droop in the steady state step response, that is, no balun.

BRIEF SUMMARY

For accurate absolute soil moisture sensors, the best Time Domain Reflectometers (TDR), whether coaxial-coupled or integrated, have necessarily incorporated either a three-conductor waveguide, or a two-conductor waveguide driven by a balancing transformer (balun). The problem remains that the use of three conductors increases the insertion force required for soil moisture testing by 50% over a two-conductor system, while the use of a balun causes steady state signals to droop.

The shortcoming of each of those techniques is the use of a coaxial cable which is the source of the single-ended waveform problem. Integrating the step function generator and the waveform digitizer onto the waveguide allows for removal of the coaxial cable from the transmission line which eliminates the problem of a single-ended waveform. The result is a balanced, differential step function applied directly to a two-conductor transmission line, a differential waveguide. Described here are methods and apparatus for accomplishing the required ultra fast, high-resolution digitization of the differential waveform.

BRIEF DESCRIPTION OF THE DRAWINGS

The particular features and advantages of the system and methods briefly described above as well as other objects will become apparent from the following description taken in conjunction with the accompanying drawings, in which.

Figure 1:
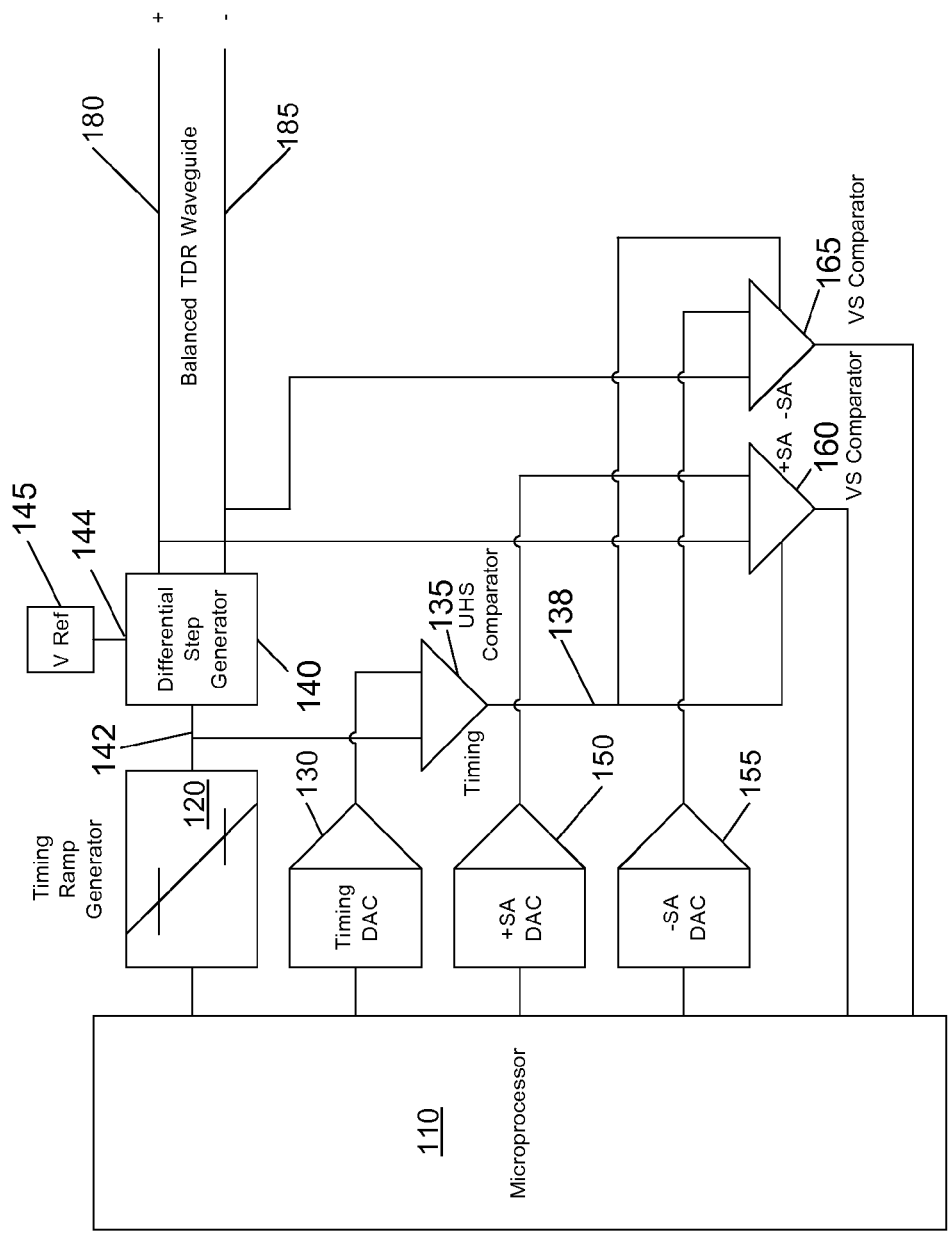
FIG. 1 is a block diagram of a differential Time Domain Reflectometer.

The following Reference Numbers may be used in conjunction with one or more of the accompanying FIGS. 1-4 of the drawings:
100 Integrated Time Domain Reflectometer
110 Microprocessor
120 Timing Ramp Generator
130 Timing Digital-to-Analog Converter (DAC)
135 Ultra High Speed Comparator, timing
138 Latch Strobe
140 Differential Step Generator
142 input to Differential Step Generator 144 reference input to Differential Step Generator
145 Voltage Reference
150 Successive Approximation DAC, positive
155 Successive Approximation DAC, negative
160 Ultra High Speed Latching Comparator, positive
165 Ultra High Speed Latching Comparator, negative
180 Balanced TDR Waveguide, positive
185 Balanced TDR Waveguide, negative
210 voltage ramp from Timing Ramp Generator
310 Incident Wave
320 Reflected Wave
330 Region of Ambiguity
470 Probe Tip
472 base of Probe Tip
475 Threaded Protrusion
480 Transmission Line Rod
482 Tapped Recess of Transmission Line Rod

DETAILED DESCRIPTION

An ideal Time Domain Reflectometer (TDR) waveguide system would employ a balanced differential wave having uniform electromagnetic (EM) field characteristics relative to the poles of the transmission line. It would accomplish this without the use of a balancing transformer (balun) in order to avoid droop in the steady state step response. For use in moisture sensing applications, it would also require no more than two rods in order to ease insertion into the media being measured and to provide a higher sampling volume.

These objectives have not been attained in a traditional coaxial-coupled Time Domain Reflectometer. The integrated TDR disclosed in U.S. Pat. No. 6,831,468 also does not meet these objectives. The implementation described there can drive a 3-conductor transmission line or it can be outfitted with a balun to drive a 2-conductor transmission line just the same as a conventional coaxial cable coupled TDR. Nonetheless, an integrated TDR is a step toward achieving the above objectives.

Integration of the step function generator and the waveform digitizer onto the waveguide eliminates the source of the single-ended waveform problem, namely the coaxial cable. By eliminating the intervening cable it is possible to generate a balanced, differential step function and to apply it directly to a 2-conductor, differential transmission line. Ultra High Speed Comparators with differential outputs, such as the ADCMP606 manufactured by Analog Devices, Inc., are capable of doing this. But digitizing a differential waveform with pico-second resolution is a more difficult matter. A proven method of digitizing a repetitive, differential, ultra high speed waveform is disclosed herein.

In FIG. 1 a precision timing generator having pico-second resolution is controlled by a microprocessor 110 with relevant firmware. The timing generator comprises a Timing Ramp Generator 120, a Timing DAC 130 (Digital-to-Analog Converter), and an Ultra High Speed Comparator 135. This timing generator provides precise, programmable timing for two closely spaced events, (a) the launching of a differential step function, and (b) the sampling of that waveform at a precise, programmable time after the launch. By incrementing the programmable time offset the microprocessor 110 controls the system to acquire amplitude measurements from successive points in time until the waveform has been digitized.

A balanced, differential Step Function Generator 140 is constructed from an Ultra High Speed Comparator that offers differential outputs. The step function generator 140 drives the transmission line as a differential waveguide (180, 185). As the waveform on the upper conductor 180 of the differential waveguide increases, the waveform on the lower conductor 185 decreases at the same rate. The overall waveform is the difference between the waveforms at the upper (180) and lower (185) conductors of the differential transmission line.

The composite waveform is derived by digitizing the two half-waveforms at the incident end of the waveguide, and then taking the difference between them in the microprocessor (110). The waveforms are simultaneously, but independently, digitized using the positive and negative Ultra High Speed Comparators (160 and 165, respectively) in conjunction with the positive and negative Successive Approximation Digital to Analog Converters (DACs 150 and 155, respectively).

Figure 2:
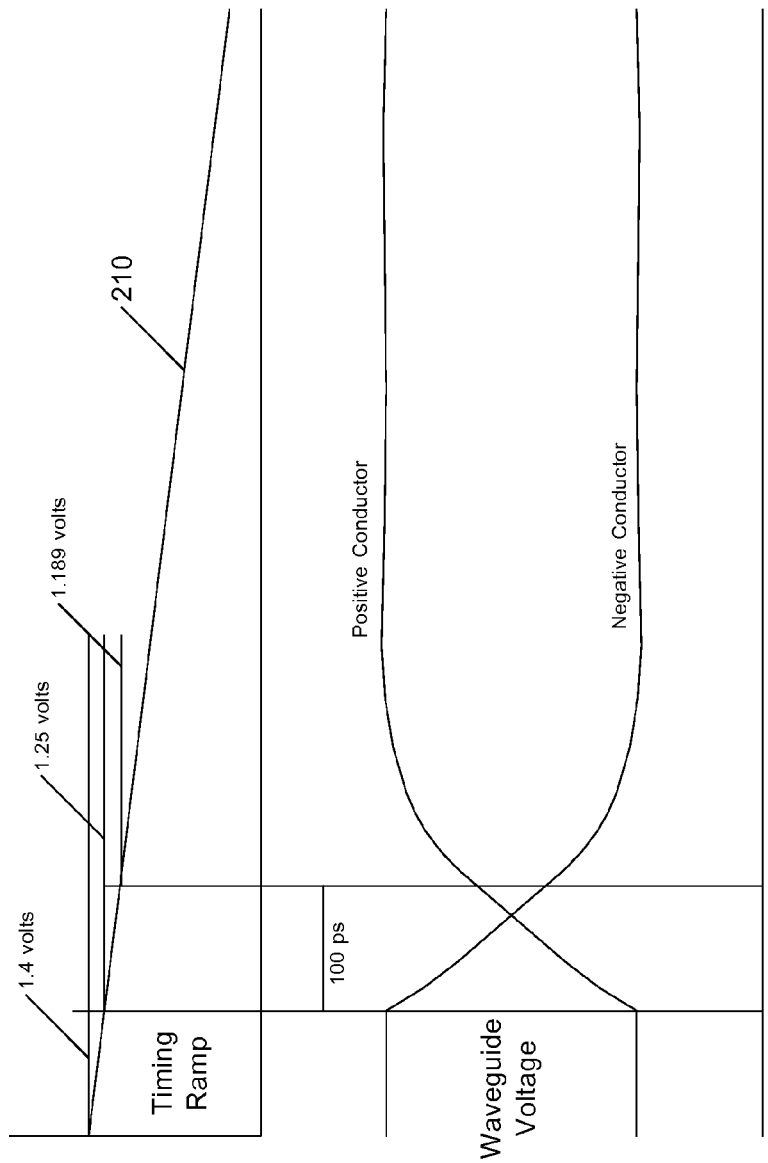
FIG. 2 shows time domain plots of launching and digitizing the differential waveform.

The process of launching and digitizing the differential waveform is described using FIG. 2. The microprocessor (110) activates the Timing Ramp Generator 120 to start a negative-slope voltage ramp 210. This ramp is generated by drawing a constant current out of a capacitor that has been pre-charged to 1.4 volts. The rate of the ramp 210 is on the order of −61 mv/ns. Thus, in 20.48 ns the ramp will traverse a range of 1.25 volts.

One of the inputs (144) of the Step Function Generator 140 is connected to a 1.25-volt reference 145, whereas the other input (142) is connected to the Timing Ramp Generator 120. When the ramp reaches 1.25 volts a differential step function is applied by the Step Function Generator 140 to the waveguide (180, 185).

The Timing DAC 130 will have been pre-set to a fixed voltage output somewhat below the 1.25-volt reference level. This Timing DAC 130 is used to generate a strobe (138) signal that will latch the state of the inputs of the Voltage Sensing Comparators 160 and 165. The output voltage of the Timing DAC 130 determines the timing of the strobe 138 relative to the launch of the waveform. For example, if the output of the Timing DAC 130 is precisely 6.1 my below the 1.25-volt reference (at 1.2439 volts), then the strobe will be generated precisely 100 psec after the launch of the step function onto the transmission line. This will cause the Voltage Sensing Comparators 160 and 165 to record the state of the waveform relative to their reference inputs at precisely 100 psec after the waveform launch. The microprocessor (110) then reads the outputs of the Voltage Sensing Comparators (160 and 165) to determine whether the positive and negative halves of the waveform were above or below the threshold settings at the comparator inputs at the 100 psec point in time.

By launching the waveform repetitively and changing the threshold settings of the Successive Approximation DACs (150 and 155), the waveform amplitude on the positive conductor 180 and the waveform amplitude on the negative conductor 185 can be separately determined. In the example of FIG. 2 the amplitude is being acquired at 100 psec. The difference between the positive and negative conductor readings is the overall differential waveform amplitude. After the waveform is measured at the 100 psec point as in FIG. 2, the Timing DAC 130 can be decremented by 305 microvolts, that is, five percent of 6.1 mV, in order to apply the successive approximation process to capture the waveform amplitude at 105 psec.

It should be noted that the successive approximation process requires a waveform launch for each bit in the resolution of the Successive Approximation DACs (150 and 155). If 12-bit DACs are used then 12 waveform launches are required to digitize a given time point on the waveform. Given that a statistically sound reading is desired each point may be digitized a number of times and each point might require more than 100 waveform launches. In order to minimize the waveform acquisition time, positive and negative halves of the differential signal are digitized simultaneously. This requires the use of two Successive Approximation DACs. It should be clear that a single DAC could be used to digitize both halves of the waveform though such a sequential procedure would require twice as much time.

Figure 3:
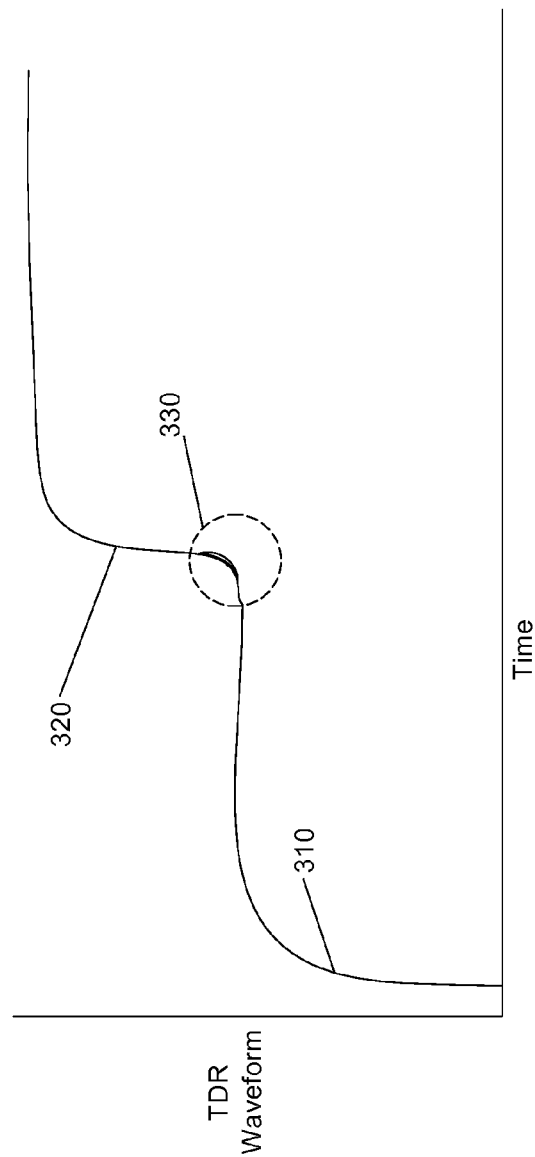
FIG. 3 is a time domain plots showing the detail at a point of ambiguity in the waveform.
Figure 4:
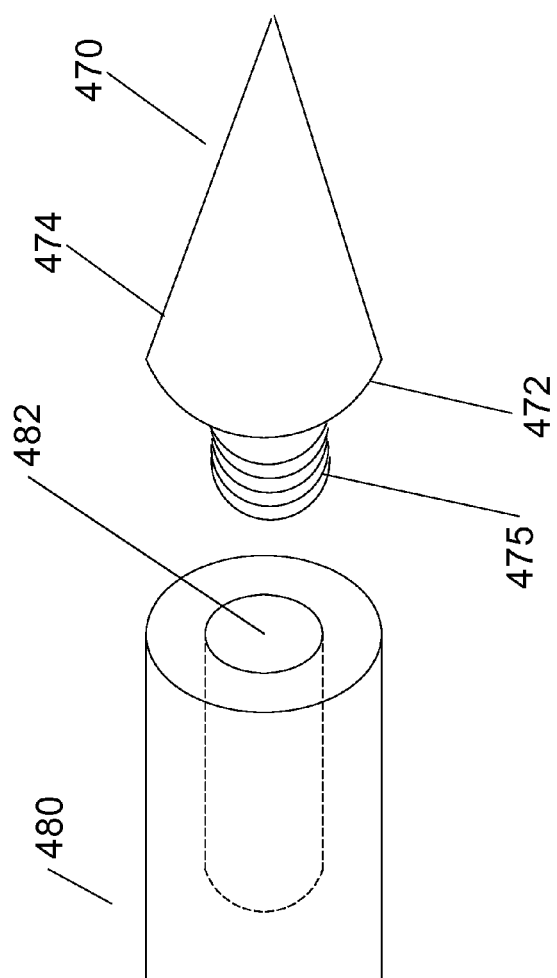
FIG. 4 depicts a two-prong probe having pointed non-conductive tips.

Referring to FIG. 3, when the step function waveform is initially applied to the TDR transmission line, the measured response tends to track the Incident Wave 310 establishing a baseline reference level. As time passes the step function reaches the open distal end of the transmission line and the Reflected Wave 320 is superimposed on top of the baseline reference level of the outbound Incident Wave 310. It is this region of the waveforms that carries information that is useful for determining the propagation time though the medium. The propagation time then may be used to calculate a bulk dielectric constant of the medium. The characteristic slope of transition in this region is useful to determine a value for the conductivity of the medium For determination of the propagation time of a waveform through a medium, alternate methods may be used. One alternate method requires taking the first and second derivatives of the waveform during the time in which the two step functions are superimposed. Due to finite rise times and losses in the medium, the two step functions no longer appear as rectangular. However, at the onset of first energy transmission in the Incident Wave 310 and at the onset of first energy reception in the Reflected Wave 320 there is a positive inflection point where the waveform turns abruptly upward from a baseline reference level. This inflection point is accompanied by a large peak in the second derivative. Noise can also create large peaks in the second derivative, but noise will not be followed by a sustained rise in the resultant waveform. That sustained rise is accompanied by a sustained positive first derivative.

In order to more quickly derive the propagation time, the waveform can be digitized at coarse timing resolution, for example, at intervals of 200 psec. Differences between adjacent amplitudes can be calculated to form the first derivative of the waveform. Differences between adjacent points of the first derivative are then taken to form the second derivative. The second derivative is examined to find peak values that are followed by sustained positive values in the first derivative. The points where this occurs are the points of the inflection points of the incident wave and of the reflected wave to within 200 psec accuracy. That is, a first pass series of measurements is made for the purpose of differentiating the waveform to locate a local maximum in a second derivative that is followed by a sustained positive value in a first derivative to establish an approximate time of an incident wave and an approximate time of a reflected wave. After these points are identified at 200 psec accuracy, further examination of the region of the waveform surrounding these points is made by acquisition of additional data at 5 psec resolution to determine the location and to establish the time of the inflection points with an accuracy of 5 psec. In other words, a second pass of measurements is made for the purpose of recalculating the time of the first derivative and the time of the second derivative of the waveform using minimal increments of the programmable time offset respectively from the approximate time of the incident wave and the approximate time of the reflected wave to determine a precise time of the incident wave and a precise time of the reflected wave.

In addition to the propagation time, another parameter of interest is the electrical conductivity of the medium. One method of determining conductivity relies upon the characteristic slope of transition which has been described in U.S. Pat. No. 6,831,468.

Another method depends upon the long-term, steady state, response of the reflected wave. This latter method was not an available option when using a single-ended TDR, or any system that included a coaxial cable, since the long-term step response would droop rapidly. The presently described differential system with an integrated TDR does not suffer from this shortcoming. Since droop is no longer a factor, conductivity may be derived from the steady state level of the reflected wave 320.

A critical part of the waveform measurement is the timebase against which the amplitude points are referenced. The accuracy of the timebase, which is described here as based upon an analog ramp, is limited by the tolerances of the components involved. High accuracy can be obtained by comparing the measured waveform propagation time with the theoretically-derived value. The difference between the two values can be used to calculate a scale factor that is then applied to the propagation readings to correct for small errors caused by component tolerances. Those skilled in the arts will recognize that other methods of generating a programmable time offset are possible including those using ultra high speed counters driven by crystal controlled frequency synthesizers. Some of these methods do not require calibration as they are crystal controlled. The system described here provides the necessary accuracy at much lower cost.

A customary feature of most TDR transmission lines used with conventional coaxial cable coupled equipment is a pointed tip on the end of the probe conductors. This greatly helps with inserting the probe into the soil, but with the high resolution possible with the circuit described above the sharpened tips become a problem.

The problem arises when the step function waveform approaches the distal end of the transmission line. As the step function waveform encounters a changing conductor diameter due to the sharpened tips a soft reflection of the waveform is produced rather than an abrupt one. The characteristic impedance near the tip is a function of the taper in the diameter. Reflections begin where the taper begins and continue to occur until the pointed tip of the conductor is reached. The net result is a region of ambiguity 330 at the onset of the reflected wave as shown in FIG. 3.

This ambiguity has a slight impact on the accuracy of determining the propagation time. If the rod tips are blunt the ambiguity is not present, but the probe is difficult to push into the soil. A solution to this problem is to fabricate the waveguide rods as in FIG. 4 with blunt tips and then to fasten a non-conductive, sharpened tip to the ends of the rods. This new probe tip 470 with a threaded stub can be screwed into a tapped hole in the end of the transmission line rod 480. It can be made of plastic, ceramic or other non-conductive material with relatively low permittivity. The probe tip 470 is fabricated in the form of a cone 474 and tapered so that the base 472 of the cone 474 has the same diameter as the transmission line rod 480, which serves as a waveguide conductor. A threaded protrusion 475 extends from the base 472 of the cone 474 so that the probe tip 470 can be screwed into a tapped recess 482 in the end of the waveguide conductor.

Although the presently disclosed apparatus has been described as a Time Domain Reflectometer for determination of absolute moisture content based upon permittivity of a medium such as soil, it will be recognized by those skilled in the related arts that the described apparatus and methods have applications in other fields, and that details of the above-described embodiments may be modified without departing from the underlying newly described principles. For example, the described apparatus and methods apply where the medium is bulk grain, bulk paper, baled hay, a hydrocarbon fuel, or oil, among other media. The scope of the present disclosure should, therefore, be determined only by the following claims.

What is claimed is:

1. A method of digitizing a waveform transmitted through a medium, which comprises:
   (a) launching a fast-transitioning differential waveform onto a proximal end of a two-conductor transmission line that passes through the medium to an open distal end of the transmission line;
   (b) receiving resultant waveforms from the two conductors using latching comparators at the proximal end of the transmission line, wherein the resultant waveforms contain signal components reflected from the open distal end of the transmission line; and
   (c) digitizing the resultant waveforms by generating timing strobes to latch the latching comparators at a programmed point in time and to measure an amplitude by a successive approximation process, wherein the digitizing comprises:
      (c1) providing a programmable time offset for generation of a precisely-timed sampling strobe offset from the launching of the fast-transitioning differential waveform to sample an amplitude of the resultant waveforms at the latching comparators;
      (c2) using the latching comparators to compare the resultant waveforms to a programmable voltage reference;
      (c3) launching a multiplicity of the fast-transitioning differential waveform onto the two-conductor transmission line and adjusting the programmable voltage reference using the successive approximation process until an amplitude representative of a composite of resultant waveforms at a point in time has been acquired; and
      (c4) incrementing the programmable time offset and repeating steps (c1) through (c3) to acquire another amplitude representative of a multiplicity of resultant waveforms until the waveform has been digitized, and wherein propagation time of the fast-transitioning differential waveform through the medium is calculated from the fast-transitioning differential waveform by a method that comprises:
      differentiating the fast-transitioning differential waveform to locate a local maximum in a second derivative that is followed by a sustained positive value in a first derivative to establish an approximate time of an incident wave and an approximate time of a reflected wave; and
      recalculating the time of the first derivative and the time of the second derivative of the fast-transitioning differential waveform using minimal increments of the programmable time offset respectively from the approximate time of the incident wave and the approximate time of the reflected wave to determine a precise time of the incident wave and a precise time of the reflected wave.

2. The method in claim 1, wherein the propagation time is used to calculate a bulk dielectric constant of the medium in contact with the transmission line.

3. The method in claim 1, wherein the precise time of the incident wave and the precise time of the reflected wave are used to calculate a characteristic slope of transition to determine conductivity of the medium in contact with the transmission line.

4. The method in claim 1, wherein a steady state value of the waveform is measured, and the steady state value is used to calculate electrical conductivity of the medium.

5. The method in claim 1, wherein the medium is moisture bearing.

6. The method in claim 1, wherein the medium is soil.

7. The method in claim 1, wherein the medium is bulk grain.

8. The method in claim 1, wherein the medium is bulk paper.

9. The method in claim 1, wherein the medium is baled hay.

10. The method in claim 1, wherein the medium is a hydrocarbon fuel.

11. The method in claim 1, wherein the medium is oil.

* * * * *